(12) United States Patent
Schneider et al.

(10) Patent No.: US 9,228,863 B2
(45) Date of Patent: Jan. 5, 2016

(54) RETRACTABLE ASSEMBLY

(71) Applicant: Endress + Hauser Conducta Gesellschaft für Mess- und Regeltechnik mbH + Co. KG, Gerlingen (DE)

(72) Inventors: Felix Schneider, Dresden (DE); Thomas Pfauch, Leipzig (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 14/677,015

(22) Filed: Apr. 2, 2015

(65) Prior Publication Data

US 2015/0285663 A1      Oct. 8, 2015

(30) Foreign Application Priority Data

Apr. 3, 2014   (DE) .................... 20 2014 101 580 U

(51) Int. Cl.
*G01F 15/14*   (2006.01)
*G01D 11/24*   (2006.01)

(52) U.S. Cl.
CPC .................................. *G01D 11/245* (2013.01)

(58) Field of Classification Search
CPC ....................................................... G01F 15/14
USPC ........................................................ 73/431
See application file for complete search history.

(56) References Cited

U.S. PATENT DOCUMENTS

| | | | |
|---|---|---|---|
| 2011/0230701 A1* | 9/2011 | Simon ................ | A61N 1/36021 600/9 |
| 2013/0036843 A1* | 2/2013 | Pfauch ................ | G01D 11/245 73/866.5 |
| 2013/0218106 A1* | 8/2013 | Coston .................. | A61B 5/207 604/317 |
| 2013/0291633 A1* | 11/2013 | Kundscher .............. | G01F 15/14 73/273 |
| 2014/0298901 A1* | 10/2014 | Wunderlich ............ | G01F 15/14 73/273 |

* cited by examiner

*Primary Examiner* — Lisa Caputo
*Assistant Examiner* — Jamel Williams
(74) *Attorney, Agent, or Firm* — Bacon & Thomas, PLLC

(57) ABSTRACT

A retractable assembly for immersion-, flow- or add-on measuring systems in analytical process technology for measuring at least one measured variable of a medium in a containment, comprising: an essentially cylindrical housing; an immersion tube, which is movable axially in the housing between a service position out of the medium and a process position in the medium; and a sensor for measuring the measured variable. The sensor is arranged in the immersion tube, wherein the sensor protrudes at least sectionally out of the immersion tube at the end of the immersion tube remote from the medium; and an openable and closable cover, which surrounds at least the section of the sensor protruding out of the immersion tube. The sensor in the opened state of the cover is mountable and demountable, respectively, in and from the immersion tube. The retractable assembly is characterized in that the cover at least sectionally travels with the movement of the immersion tube and in the process position is located at least sectionally in the housing.

11 Claims, 5 Drawing Sheets

RETRACTABLE ASSEMBLY

TECHNICAL FIELD

The invention relates to a retractable assembly for immersion-, flow- and add-on measuring systems, especially in analytical process technology for measuring at least one measured variable of a medium.

BACKGROUND DISCUSSION

Retractable assemblies are widely applied in analytical measurements technology. They serve to withdraw sensors from the process, and therewith from the medium, without process interruption and then to reintroduce them back into the process. The sensors are held in an immersion tube and moved by means of a drive manually or automatically, for example, pneumatically, axially between a process position and a service position. These procedures run within a determined timing cycle or as a function of other determinable or measured parameters.

Sensors for use in this invention include sensors for measuring one or more physical or chemical, process variables.

If retractable assemblies are used for accommodating the sensor for determining at least one process variable, the sensor can be checked, calibrated, cleaned and/or replaced in the service position, wherein the sensor is located, in such case, in a handling chamber arranged in the housing of the retractable assembly.

Retractable assemblies are manufactured and sold by the group of firms, Endress+Hauser, for example, under the mark/designation, "Cleanfit H CPA475".

The field of use of retractable assemblies for measuring physical or chemical, process variables of a medium, e.g. a fluid, especially a liquid, in process technology is all encompassing. Used for determining the process variables are sensors, examples of which include pH sensors, conductivity sensors, optical or electrochemical sensors for determining a concentration of a substance contained in the medium to be monitored, e.g. substances such as $O_2$, $CO_2$, certain ion types, organic compounds, or the like. The medium can, in given cases, be a critical medium. The terminology, critical, means, for instance, that the medium is valuable, expensive, combustible, corrosive, poisonous, aggressive, hot, cold, bio-endangering, radioactive, etc.

In all cases, it is to be heeded that no medium escapes from the process. Especially, care must be taken that the sensor is not deinstalled when the retractable assembly is located in the process position, since otherwise a connection from the process to the environment is created.

SUMMARY OF THE INVENTION

An object of the invention is to prevent, in a simple manner, sensor deinstallation in the process position.

The object is achieved by a retractable assembly for measuring at least one measured variable of a medium in a containment, comprising: an essentially cylindrical housing; an immersion tube, which is movable axially in the housing between a service position out of the medium and a process position in the medium; a sensor for measuring the measured variable, wherein the sensor is arranged in the immersion tube, wherein the sensor protrudes at least sectionally out of the immersion tube at the end of the immersion tube remote from the medium; and an openable and closable cover, which surrounds at least the section of the sensor protruding out of the immersion tube; wherein the sensor in the opened state of the cover is mountable and demountable, respectively, in and from the immersion tube. The retractable assembly is characterized in that the cover at least sectionally travels with the movement of the immersion tube and in the process position is located at least sectionally in the housing.

Preferably, the cover is so embodied, in such case, that it cannot be opened, when the immersion tube is located in the process position. A sensor deinstallation can, thus, be prevented. Consequently, it is not possible for process medium to leave the process and reach the environment.

In an advantageous embodiment, the cover includes on its end facing the medium an essentially cylindrical section, whose diameter is less than the diameter of the section of the housing, into which the cover moves. In other words, the outer diameter of the immersion tube is less than the inner diameter of the housing at the respectively relevant locations. Thus, the cover can move into the housing.

In a preferred form of embodiment, the cover is essentially cylindrically embodied and includes a first half shell as well as a second half shell. In such case, the first half shell and the second half shell are connected with one another via a shared edge. The cover can, thus, be simply opened.

In an advantageous embodiment, the cover is manufactured of a synthetic material, e.g. a plastic. Preferably, the synthetic material is embodied to be antistatic. In this way, the retractable assembly can be applied in the Ex-region.

In an advantageous embodiment, the immersion tube includes on its end remote from the medium a first conical section with smaller diameter toward the medium, and the cover includes a second conical section corresponding to the first conical section, wherein a web pointing into the interior of the cover is placed on the process remote end region of the second section, and wherein the second conical section surrounds the first conical section. In this way, the cover can be secured to the immersion tube.

Preferably, the movement from service position to process position and vice versa is effected by means of an energy supply, especially pressurized air. In this way, the movement of the immersion tube can occur automatically, for example, at certain intervals.

Alternatively or supplementally, the movement from service position into process position and vice versa is effected by means of a hand drive, especially by means of a manual spindle drive. This is a simple and cost effective manner of moving the immersion tube.

In an advantageous embodiment, the cover includes a holder for a tool, especially a wrench, preferably an open-ended wrench or a socket wrench, wherein the tool is so embodied that therewith at least the sensor is mountable or demountable, respectively, in and from the immersion tube. This saves a service technician time, since a suitable tool is always available.

Preferably, the cover includes, especially on its end remote from the medium, a cable- and/or hose guide.

In an advantageous form of embodiment, the cover includes, especially on its end remote from the medium, a hook. By means of the hook, the cover can, in the case of service work on the already mentioned cable or the like, be hung up, in order therewith to provide a tidy workspace.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
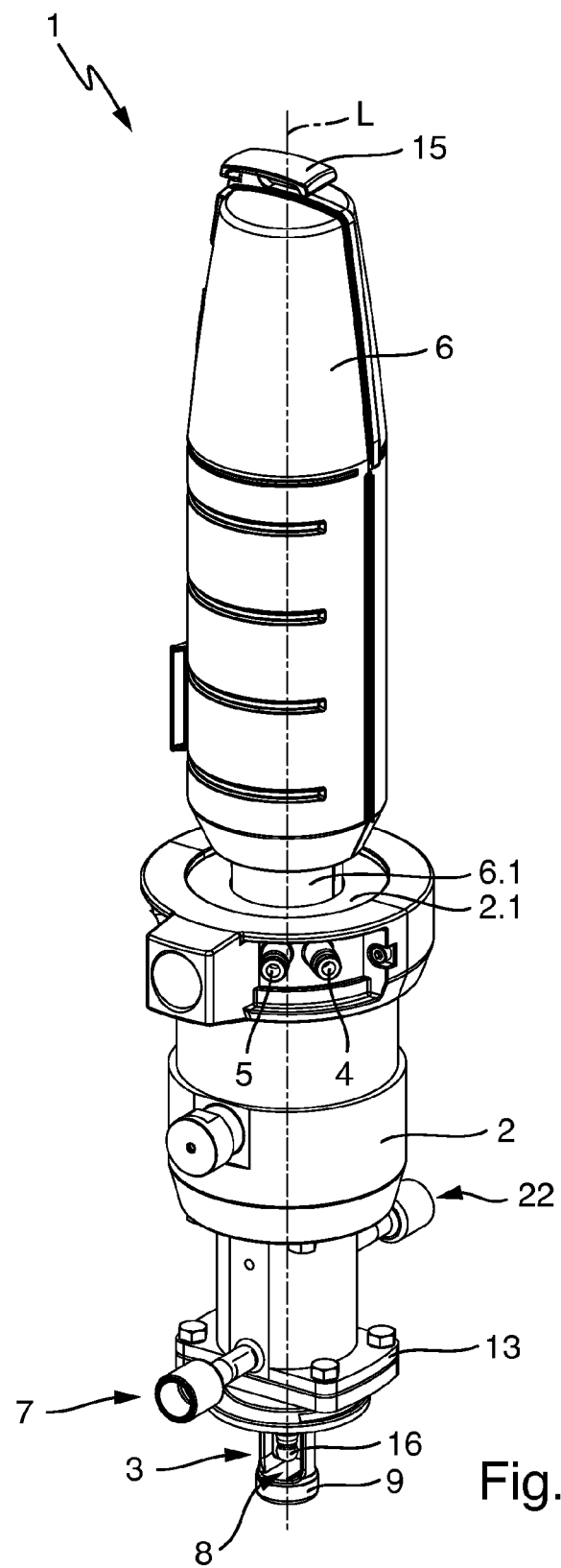
FIG. 1 is a general view of the retractable assembly of the invention in the process position.

In the figures, similar features are provided with similar reference characters.

"Up", "above" and related terms mean in the sense of this invention away from the medium, while "down", "below" and related terms mean toward the medium in the sense of the invention.

The retractable assembly of the invention in its totality is given the reference character 1 and is shown in FIG. 1. Retractable assembly 1 is composed of an essentially cylindrical housing 2, which can be connected by means of a connecting means 13 to a containment (not shown). Connecting means 13 can be, for instance, a flange connection, e.g. of stainless steel. Other embodiments are, however, possible. Located in the containment is the medium to be measured. The containment can be, for instance, a container, vat, pipe, pipeline or the like.

FIG. 1 shows the retractable assembly 1 in the process position. This is explained in the following in greater detail.

Guided within the housing 2 is an immersion tube 3. A sensor 16 is connected with the immersion tube 3 by way of a receptacle (not shown), for example, by a screwed connection. The sensor 16 in the sense of this invention is a sensor for measuring one or more physical or chemical, process variables. Among these are, for example, pH-value, also via an ISFET, redox-potential, absorption of electromagnetic waves in the medium, for example, with wavelengths in the UV-, IR-, and/or visible region, oxygen, conductivity, turbidity, concentration of metal and/or non-metal substances, or temperature. Via an opening 8 in the immersion tube 3, the sensor 16 has access to the medium to be measured. In such case, the opening 8 is so embodied that it is open to flow, especially when the retractable assembly 1 is applied in a pipeline, i.e. such that the sensor 16 is optimally flowed on by the medium.

The immersion tube 3 can be produced of different materials, examples being steel and stainless steel. There are, however, applications, especially in the chemical industry, in the case of which very resistant materials are applied. The immersion tube 3 can, thus, also be made of a synthetic material, such as polyetheretherketone (PEEK), polytetrafluoroethylene (PTFA), a perfluoroalkoxy-polymer (PFA), some other synthetic material or resistant metals such as, for instance, Hastelloy. The same holds for housing 2.

The immersion tube 3 is held axially displaceably for movement toward and away from the medium along the central axis A. The immersion tube 3 is, in such case, movable between the service position in the housing 2 and the process position (shown in FIG. 1), in which it protrudes out of the housing 2. Measuring takes place in the process position, while in the service position the most varied of service tasks, such as cleaning or calibration, are performed. Through connection 7, cleaning, rinsing, washing and calibration liquid can be introduced into the housing interior, especially into the service chamber 11. Through outlet 22, which can be positioned offset both axially as well as also radially from the connection 7, liquid can be drained away. Also, the rinse, wash direction can be reversed.

The shifting of the immersion tube 3 is effected by a manual, spindle drive or an automatic drive, for instance, by means of an energy supply. If the energy supply is introduced through the connection 4, the immersion tube 3 moves from the service position into the process position. The connection 5 serves then as outlet for the energy supply. If the energy supply is introduced through the connection 5, the immersion tube 3 moves from the process position into the service position. The connection 4 then serves as outlet. Known from the state of the art are, for example, pneumatic, hydraulic or electrical drives. In FIG. 1, the two connections 4 and 5 are arranged next to one another, An embodiment with connections 4 and 5 arranged on top of one another is, however, also possible, such as shown, for instance, in FIG. 5.

In the case of a manual, spindle drive, starting from the service position, rotation of a spindle nut in the clockwise direction moves the immersion tube 3 into the process position. Also the hand drive can only be moved with mounted sensor 16 into the process position. Without screwed-in sensor, the drive is blocked. Upon reaching the process position, a lock engages, so that the drive cannot drift out of the process position. Only by manually unlocking the lock can the manual drive move the immersion tube 3 back into the service position. In the service position, there is no lock, but a drifting of the sensor is, nevertheless, prevented by the self-limiting spindle drive. In a special embodiment, a self-limiting, multi-start screw thread, especially a trapezoidal thread, is used. The upper end of the immersion tube 3 is exactly so embodied as in the case of a retractable assembly 1 operated with an energy supply and is surrounded by the cover 6. A sensor removal in the process position is also prevented thereby in the case of a manual drive.

If the immersion tube 3 is in the service position, a portion of the immersion tube 3, especially the sensor 16, is located in the housing interior, in the so-called service chamber 11, for rinsing, cleaning, calibrating, etc. Located on the lower end of the immersion tube 3 for sealing off of the process is the closure element 9. Closure element 9 seals the service chamber 11 from the process, and therewith from the medium. The medium can be hot, poisonous, corrosive or in other manner damaging for humans and the environment. It is, consequently, to be heeded that the closure element 9 safely and durably seals. For such purpose, different sealing systems are provided on the housing 2. Especially, one or more seals 10 are used.

Figure 4:
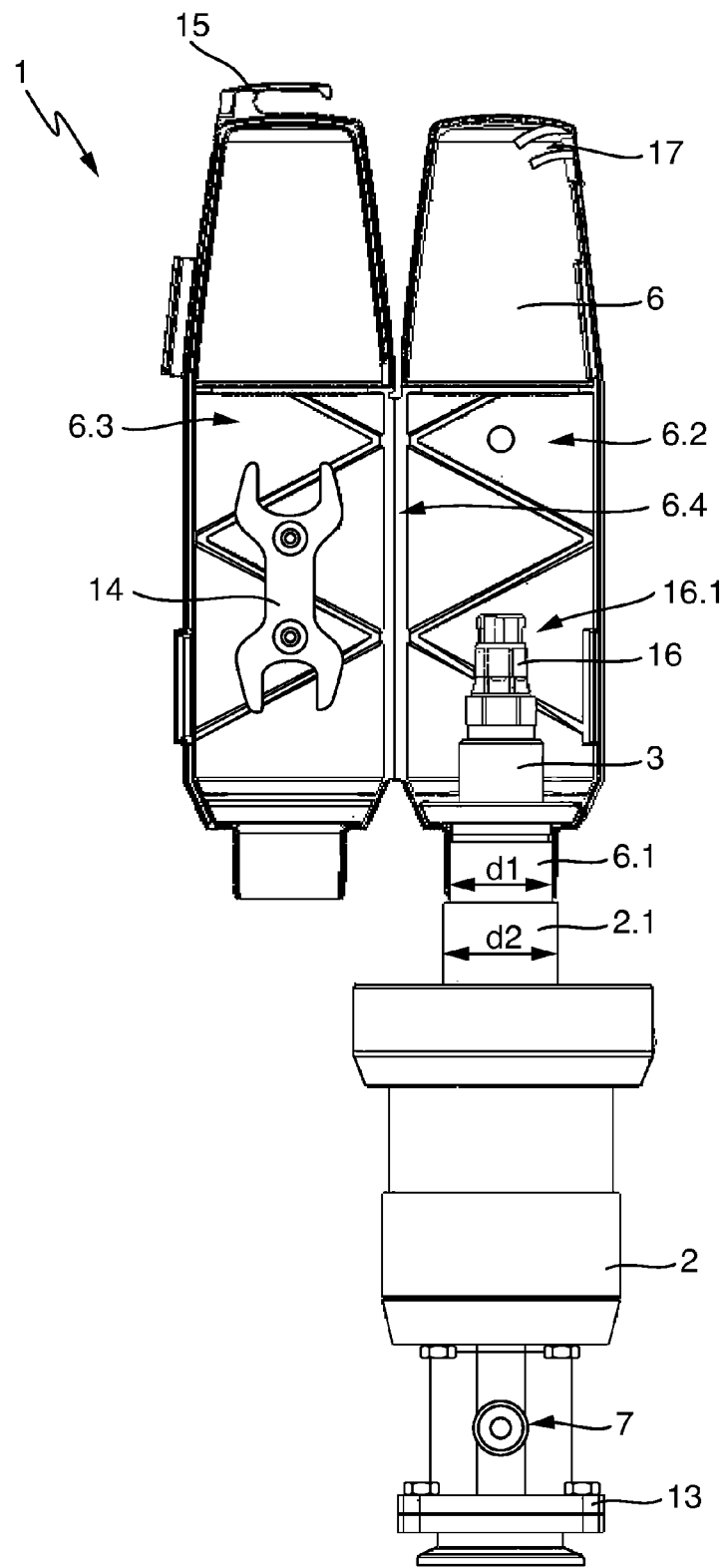
FIG. 4 the opened cover in the case of a retractable assembly in the service position.

Placed on the end of the retractable assembly 1 remote from the medium for the protection of the sensor 16 is a cover 6. Cover 6 is manufactured, for instance, of a polymer, for example, polypropylene. The applied synthetic material is embodied to be antistatic and can, thus, be used in the Ex-region. As especially evident in FIG. 4, the sensor 16 protrudes somewhat from the immersion tube 3. The protruding section is provided with the reference character 16.1. Cover 6 protects the protruding section 16.1 from dirt, cold weather, moisture, precipitation, and, in general, from external influences.

Cover 6 is so embodied that it is openable and closable. In the opened state (compare FIG. 4), the sensor 16 can be removed from the immersion tube.

Cover 6 is, as mentioned, essentially cylindrically embodied and includes a first half shell 6.2 as well as a second half shell 6.3. First half shell 6.2 and second half shell 6.3 are connected with one another via a shared edge 6.4. The second half shell 6.3 can via the shared edge 6.4 be swung open, respectively away, from the first half shell 6.2.

The immersion tube 3 includes on its end remote from the medium a first conical section 18 with smaller diameter toward the medium. Cover 6 includes a second conical section 19 corresponding to the first conical section 18 of the immersion tube 3, wherein the second conical section 19 surrounds the first conical section 18, when the cover 6 is located in its closed state. Located on the process remote end region of the second section 19 is a web 20 pointing into the interior of the cover 6. In this way, the cover 6 can securely engage the immersion tube.

Located on the section of the cover 6 lying opposite the shared edge 6.4 are corresponding mechanisms, for example, a "clip mechanism" or a "pin-eye mechanism" or the like on the first half shell 6.2, respectively on the second half shell 6.3, for the secure closing of the cover 6.

Figure 2A:
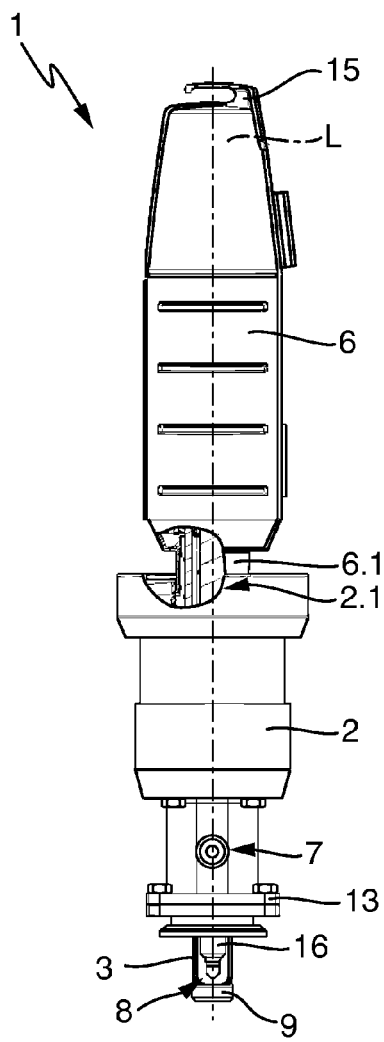
FIGS. 2a and 2b the retractable assembly of the invention in the process position with a portion of the cover in cross section, together with an enlargement of such portion.
Figure 2B:
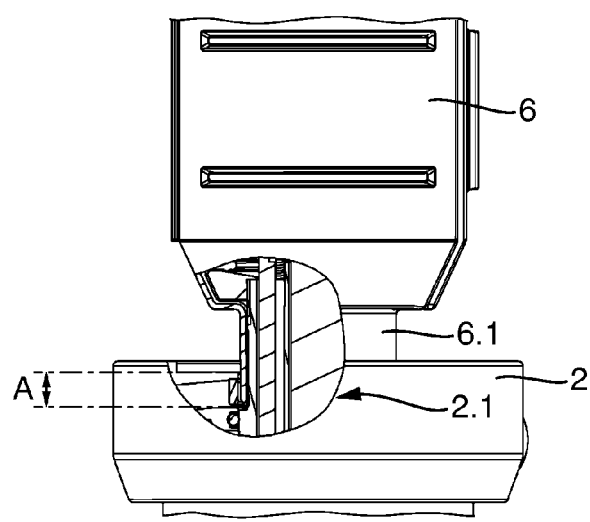
Figure 3:
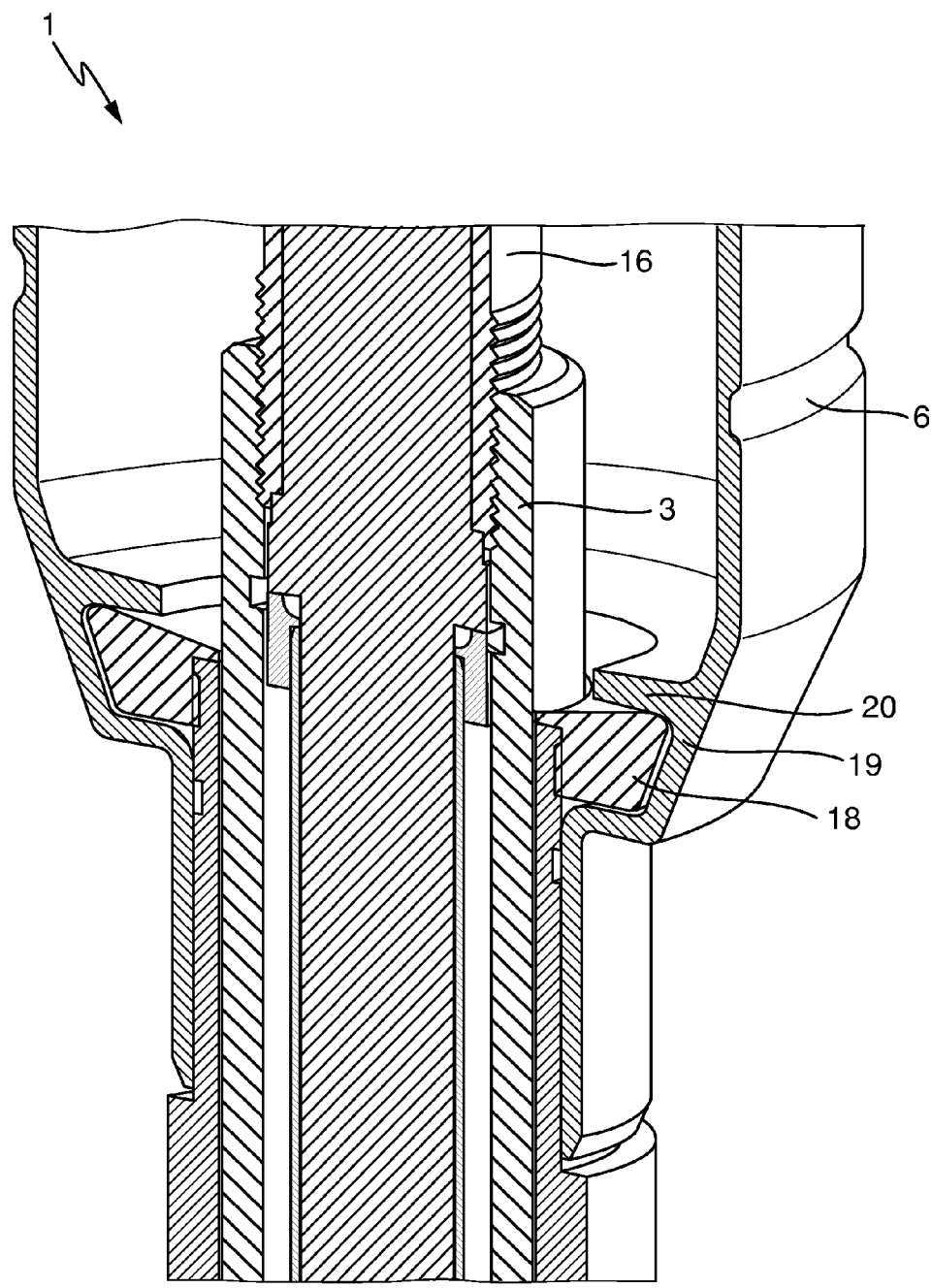
FIG. 3 is a three-dimensional view of the retractable assembly in cross section.

FIG. 2a shows the retractable assembly 1 in the process position with a portion of the cover 7 in cross section and FIG. 2b shows an enlargement of this portion.

Cover 6 includes a section 6.1 facing the medium. This section 6.1 is essentially cylindrically embodied and has a first diameter d1. In the case of movement from service position into process position, the cover 6 plunges at least partially into the housing 2, the extent of this plunging being indicated with the reference character A. The housing 2 includes an essentially cylindrical opening 2.1 with a diameter d2. The diameter d2 of the housing 2 is greater than the diameter d1 of the cover 6. The diameters d1, respectively d2, are, for example, 34 mm, respectively 35 mm.

Cover 6, respectively its section 6.1 facing the medium, is located at least sectionally in the housing 2, when the immersion tube is located in the process position. In this way, the cover 6 cannot be opened and it is impossible for the user to reach or attempt to replace the sensor. The cover can extend, for instance, 10 mm into the housing.

Included at the upper end of the cover 6 is a cable- and/or hose guide 17. Thus, in simple manner, a cable connected to the sensor 16 can be led away. Transmitted by means of the cable are data and/or energy to/from the one or more sensors. If the sensor is, for instance, embodied as a sensor with refillable liquid reservoirs (thus, for instance, a pH-sensor), the required hose can be guided by means of the cable- and/or hose guide 17.

Additionally located on the upper end of the cover 6 is a hook 15. By means of the hook 15, the cover 6 can, in the case of service work on the already mentioned cable or the like, be hung up, in order to provide a tidy situation for the work.

Further accommodated in the cover 6 can be a tool 14. The tool 14 is, for instance, a wrench, preferably an open ended wrench or a socket wrench. By means of the tool 14, for instance, the sensor 16 can mounted and demounted. Additionally, other service work can be performed therewith, such as, for instance, the multifunctional engagement means known from DE 10 2013 103 459 (US 2014/0298901 A1) can be serviced.

Figure 5:
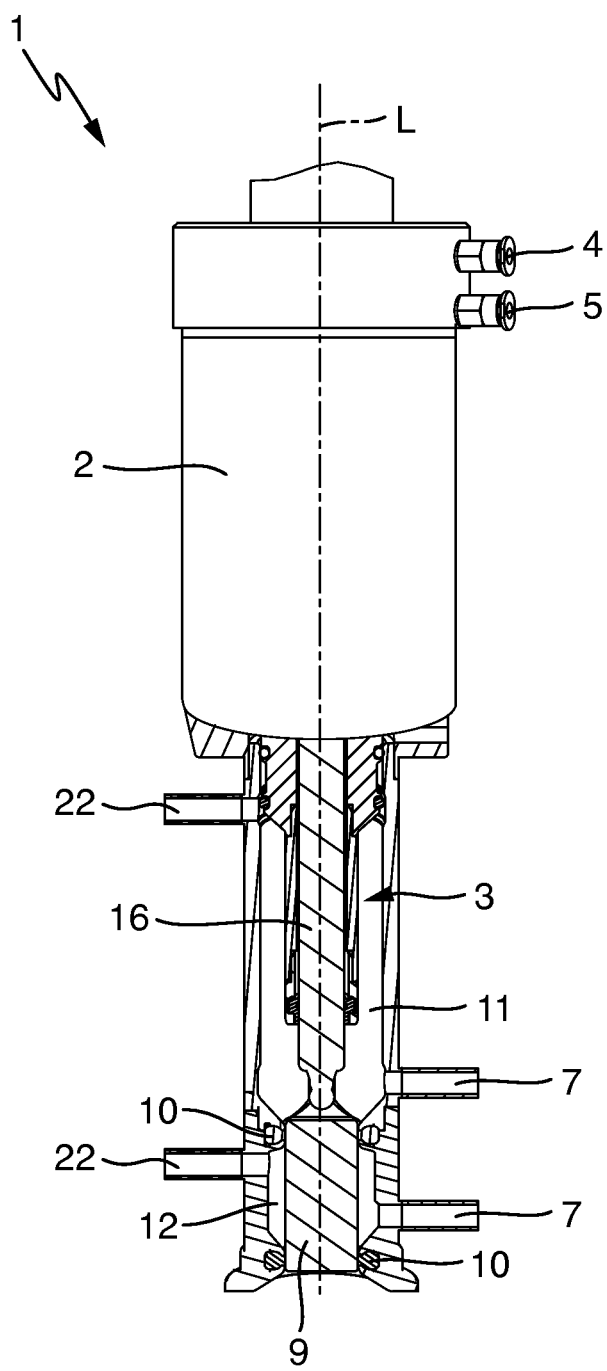
FIG. 5 a lower section of the retractable assembly of the invention with an additional rinsing/washing chamber.

Located in an embodiment shown in FIG. 5 in the housing 2 below the service chamber 11, thus between the service chamber 11 and the containment, is another chamber, the so called rinsing chamber 12. Especially in the case of hygienic applications, this chamber 12 can be utilized as a supplemental barrier between medium and service chamber 11. Counting the service chamber 11, there are then two different chambers available for performing work on the sensor. An example of such work is the sterilization or calibrating of the sensor in the service chamber 11. Other rinse, wash, connections 7, respectively 22 can be present.

The invention claimed is:

1. A retractable assembly for immersion-, flow- or add-on measuring systems in analytical process technology for measuring at least one measured variable of a medium in a containment, comprising:

an essentially cylindrical housing;
an immersion tube, which is movable axially in said housing between a service position out of the medium and a process position in the medium;
a sensor for measuring the measured variable, said sensor is arranged in said immersion tube, and said sensor protrudes at least sectionally out of said immersion tube at the end of said immersion tube remote from the medium; and
an openable and closable cover, which surrounds at least said section of the sensor protruding out of said immersion tube, said sensor in the opened state of said cover is mountable and demountable, respectively, in and from the immersion tube, wherein:
said cover at least sectionally travels with the movement of said immersion tube and in the process position is located at least sectionally in said housing.

2. The retractable assembly as claimed in claim 1, wherein:
said cover is so embodied that it is not openable, when said immersion tube is located in the process position.

3. The retractable assembly as claimed in claim 1, wherein:
said cover includes on its end facing the medium an essentially cylindrical section, whose diameter is less than the diameter of the section of said housing, into which said cover moves.

4. The retractable assembly as claimed in claim 1, wherein:
said cover is essentially cylindrically embodied and includes a first half shell as well as a second half shell; and
said first half shell is connected with said second half shell via a shared edge.

5. The retractable assembly as claimed in claim 1, wherein:
said immersion tube includes on its end remote from the medium a first conical section with smaller diameter toward the medium; and
said cover includes a second conical section corresponding to said first conical section;
a web pointing into the interior of said cover is placed on said process remote end region of said second section; and
said second conical section surrounds said first conical section.

6. The retractable assembly as claimed in claim 1, wherein:
a pressurized air energy supply, effects movement from a service position into a process position and vice versa.

7. The retractable assembly as claimed in claim 1, wherein:
movement from said service position into said process position and vice versa is effected by means of a hand drive.

8. The retractable assembly as claimed in claim 1, wherein:
said cover includes a holder for a tool, preferably an open ended wrench or a socket wrench; and
said tool is so embodied that therewith at least the sensor is mountable or demountable, respectively, in and from said immersion tube.

9. The retractable assembly as claimed in claim 1, wherein:
said cover includes, on its end remote from the medium, a cable- and/or hose guide.

10. The retractable assembly as claimed in claim 1, wherein:
said cover includes, on its end remote from the medium, a hook.

11. The retractive assembly as claimed in claim 1, wherein:
said hard drive comprises a manual spindle drive.

* * * * *